United States Patent [19]

Skerratt

[11] Patent Number: 5,258,314

[45] Date of Patent: Nov. 2, 1993

[54] MICROPROCESSOR-BASED BIOMEDICAL MONITORING APPARATUS AND METHOD

[75] Inventor: Brenda L. Skerratt, Aurora, Canada

[73] Assignee: Paradigm Biotechnologies Partnership, Canada

[21] Appl. No.: 931,453

[22] Filed: Aug. 20, 1992

Related U.S. Application Data

[63] Continuation of Ser. No. 671,200, Mar. 18, 1991, abandoned.

[51] Int. Cl.⁵ .................... G01N 21/03; G01N 21/05; G01N 35/00
[52] U.S. Cl. ......................... 436/165; 422/58; 422/66; 422/67; 422/81; 422/82.05; 422/82.09; 422/100; 422/102; 436/43
[58] Field of Search ............. 422/58, 63, 66, 67, 422/81, 82.05, 82.09, 100, 102; 436/43, 165; 206/219

[56] References Cited

U.S. PATENT DOCUMENTS

| | | |
|---|---|---|
| 3,036,894 | 5/1962 | Forestiere .................. 422/66 X |
| 3,476,515 | 11/1969 | Johnson et al. .............. 422/61 X |
| 3,699,348 | 10/1972 | Höcherl ..................... 422/65 X |
| 3,713,779 | 1/1973 | Sirago et al. ................ 422/61 |
| 3,770,382 | 11/1973 | Carter et al. ................ 422/65 |
| 3,912,452 | 10/1975 | Sodickson et al. ........... 422/81 X |
| 4,065,263 | 12/1977 | Woodbridge, III ........... 422/57 |
| 4,633,878 | 1/1987 | Bombardieri ................ 128/635 |
| 4,662,208 | 5/1987 | Metzner et al. .............. 436/178 X |
| 4,690,801 | 9/1987 | Anderson .................... 422/100 X |
| 4,708,931 | 11/1987 | Christian .................... 422/63 X |
| 4,708,940 | 11/1987 | Yoshida et al. .............. 422/100 X |
| 4,731,726 | 3/1988 | Allen, III ..................... 422/55 |
| 4,863,454 | 9/1989 | LaBove ....................... 604/416 |
| 4,897,189 | 1/1990 | Greenwood et al. .......... 210/195.2 |
| 4,916,078 | 4/1990 | Klose et al. .................. 422/72 X |
| 5,037,614 | 8/1991 | Makita et al. ................ 422/82.05 X |
| 5,073,345 | 12/1991 | Scott et al. ................... 422/82.09 X |
| 5,089,233 | 2/1992 | DeVaney, Jr. et al. ....... 422/99 |
| 5,154,888 | 10/1992 | Zander et al. ................ 422/58 |

FOREIGN PATENT DOCUMENTS

0381501 8/1990 European Pat. Off. .

*Primary Examiner*—James C. Housel
*Assistant Examiner*—Arlen Soderquist
*Attorney, Agent, or Firm*—Timothy R. Kroboth

[57] ABSTRACT

A microprocessor-based, control unit for analysis of a fluid sample, and for especially biomedical analysis of a body fluid, is provided. Also provided is the combination of a roller assembly and a compartmentalized pouch containing certain chemicals, with the rollers functioning to break rupturable seals of compartments and to push fluids from one compartment to another. Apparatus in accordance with the present invention, is useful, for example, in monitoring urea concentration during dialysis.

7 Claims, 5 Drawing Sheets

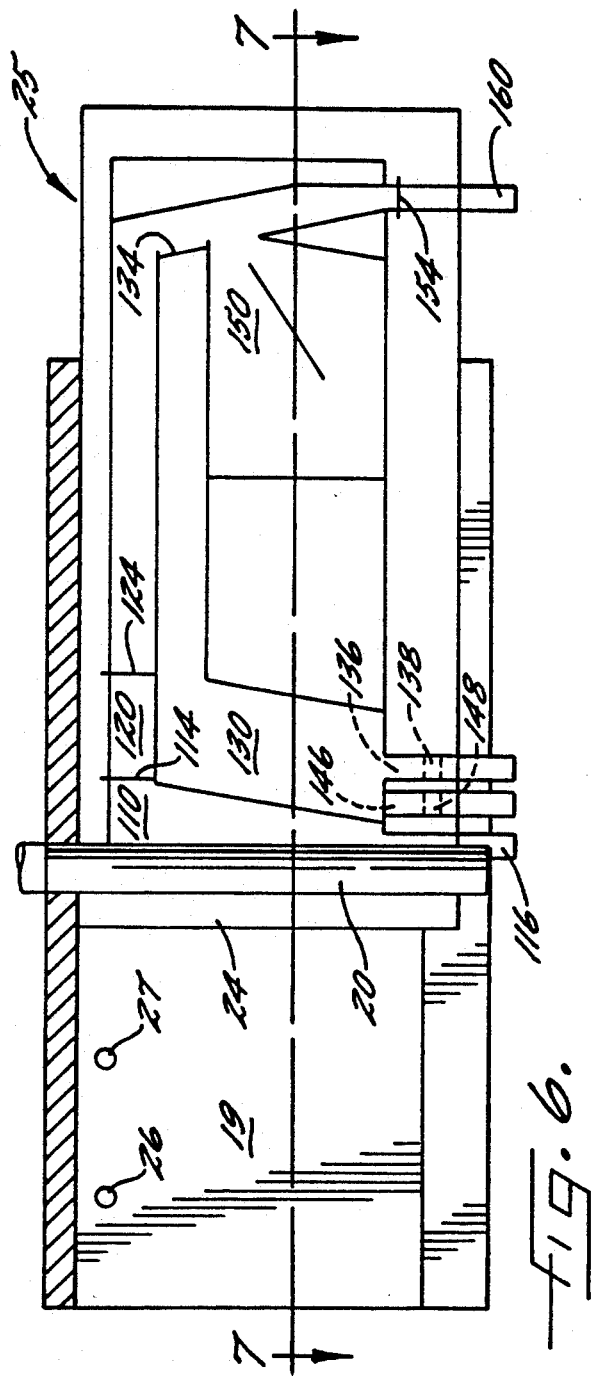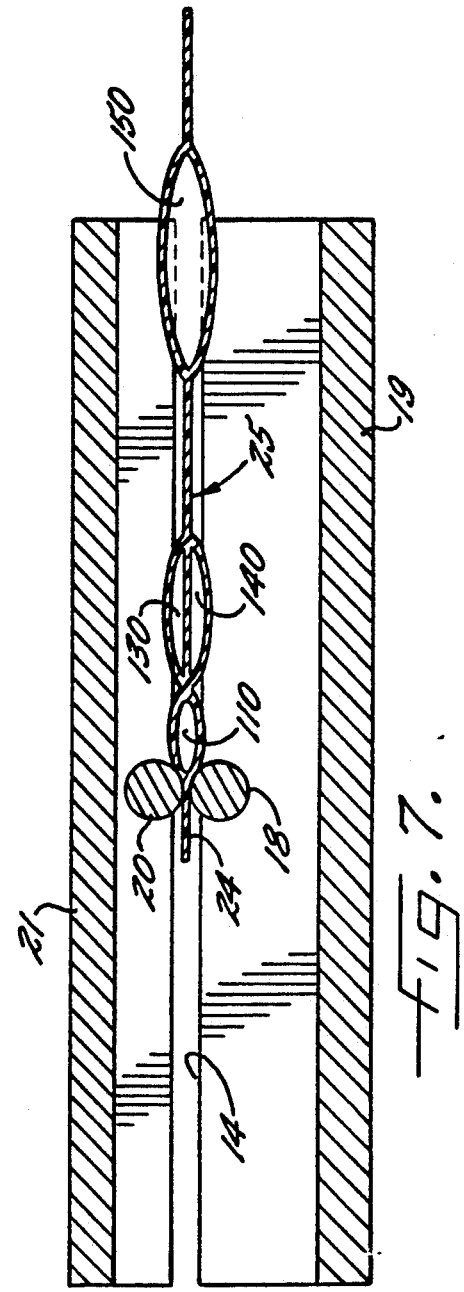

MICROPROCESSOR-BASED BIOMEDICAL MONITORING APPARATUS AND METHOD

This application is a continuation of application Ser. No. 671,200, filed Mar. 18, 1991 now abandoned.

BACKGROUND OF THE INVENTION

This invention relates generally to the analysis of a liquid sample, and especially to biomedical analysis of a body fluid such as a dialyzed body fluid.

As illustrated by U.S. Pat. No. 4,633,878 to Bombardieri, the use of a sensor to determine the concentration of a target chemical species in a liquid sample provided by a separator device such as a hollow fiber membrane, and to communicate the concentration data to a microprocessor, is known. As exemplified by U.S. Pat. No. 4,897,189 to Greenwood et al, a piston driven by a microprocessor-controlled motor, is known for pressure-compressing a compartment containing a liquid, to drive the liquid from the compartment. Additionally, as illustrated by U.S. Pat. No. 4,863,454 to LaBove, it is known to join a pair of containers with a flow connector in between, and to, by force of gravity, pass the contents of one container into the other.

However, there is a need for improved analytical apparatus useful in the analysis of a small liquid sample for a target chemical species. Such apparatus would beneficially provide for the preparation of an analyzable product, suitably a colorimetrically analyzable product, from the target species, and provide for quantitative analysis. Advantageously, such apparatus would be capable of controlling the preparation of the analyzable product, of analyzing the product, and of informing a user as to the analytical value obtained. Such apparatus would be especially beneficial for monitoring urea concentration during dialysis.

SUMMARY OF THE INVENTION

It is accordingly an object of the present invention to provide improved analytical apparatus useful in the analysis of a small liquid sample for a target chemical species.

It is a further object for such apparatus to provide for the preparation of an analyzable product from the target species.

It is a still further object for such apparatus to be capable of controlling the preparation of the analyzable product, of analyzing the product, and of informing a user as to the results obtained.

It is an even further object for such apparatus to be useful for monitoring urea concentration during dialysis.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, improved analytical apparatus is provided. The apparatus includes a compartmentalized, analysis pouch, and a roller assembly. The roller assembly advances the analysis pouch and compresses pressure-compressible compartments of the pouch.

The analysis pouch has an inlet port for receiving a fluid sample to be analyzed for a target chemical species. The fluid sample may be a body fluid. An exemplary body fluid is plasma water obtained by ultrafiltration of dialyzed blood, or is peritoneal fluid.

The inlet port of the pouch is in fluid communication with a first pressure-compressible compartment. A first rupturable seal conveniently forms a portion of a wall defining the first compartment and provides, after being ruptured suitably by roller pressure, for fluid communication with a second pressure-compressible compartment. The second compartment contains a selected quantity of a chemical for producing a reaction product upon interaction with the target chemical species.

In one preferred embodiment of the pouch, a second rupturable seal forms a portion of a wall defining the second compartment and provides, after being pressure-ruptured, for fluid communication with a third pressure-compressible compartment. Mixing of the reaction product with a reagent or reagents to produce an analyzable product, takes place in the third compartment.

In another preferred embodiment of the pouch, a second rupturable seal forms a portion of the wall defining the first compartment and provides, after being pressure-ruptured, for fluid communication with a third pressure-compressible compartment. The third compartment contains a reagent or reagents for mixing with the reaction product to produce an analyzable product.

Also provided is a microprocessor-based, control unit for analysis of a fluid sample. The control unit advantageously includes a microprocessor-controlled motor, and a roller assembly controlled by the motor, for advancing an analysis pouch through the rollers and compressing the pouch.

An essential feature of the control unit is a colorimetric analysis assembly. The assembly includes a flow cell having an inlet port connectable to an exit port of the analysis pouch for receiving a colorimetrically analyzable, colored solution from the pouch. The flow cell has a generally z-shaped pathway that includes a central path. A light source is situated at an end of the central path, and a light sensor is located at an opposite end of the central path. The microprocessor operatively communicates with the light source and the light sensor.

In the drawings and in the detailed description of the invention that follows, there are shown and essentially described only preferred embodiments of this invention, simply by way of illustration of the best mode contemplated by me of carrying out this invention. As will be realized, this invention is capable of other and different embodiments, and its several details are capable of modification in various respects, all without departing from the invention. Accordingly, the drawings and the detailed description are to be regarded as illustrative in nature, and not as restrictive.

BRIEF DESCRIPTION OF THE DRAWING

Reference is now made to the accompanying drawing, which forms a part of the specification of the present invention, and which depicts preferred embodiments of apparatus in accordance with the present invention.

FIG. 6 is partial, plan view of the assembly of FIG. 2, with the pouch of FIG. 5 in engagement with the rollers of the assembly;

FIG. 7 is a cross-sectional view taken substantially along line 7—7 of FIG. 6.

DETAILED DESCRIPTION OF THE INVENTION

The present invention is useful for analyzing small samples of a fluid, in particular a body fluid, for a target chemical species. As will become understood, the present invention is capable of drawing a selected volume of a fluid sample, providing for conversion of the target species into a reaction product, providing for reaction thereof with a suitable reagent or reagents to form an analyzable product, which is suitably a colorimetrically analyzable, colored solution, carrying out the analysis, determining the concentration of the target species from the analytical result, and informing the user of the concentration.

As will be explained, the present invention is based upon a control unit that is advantageously small in size, portable and self-contained. The present invention is further based upon the combination of a roller assembly and a compartmentalized pouch containing certain chemicals, with the rollers functioning to break temporary seals of the compartments and to push fluids from one compartment to another.

Figure 1:
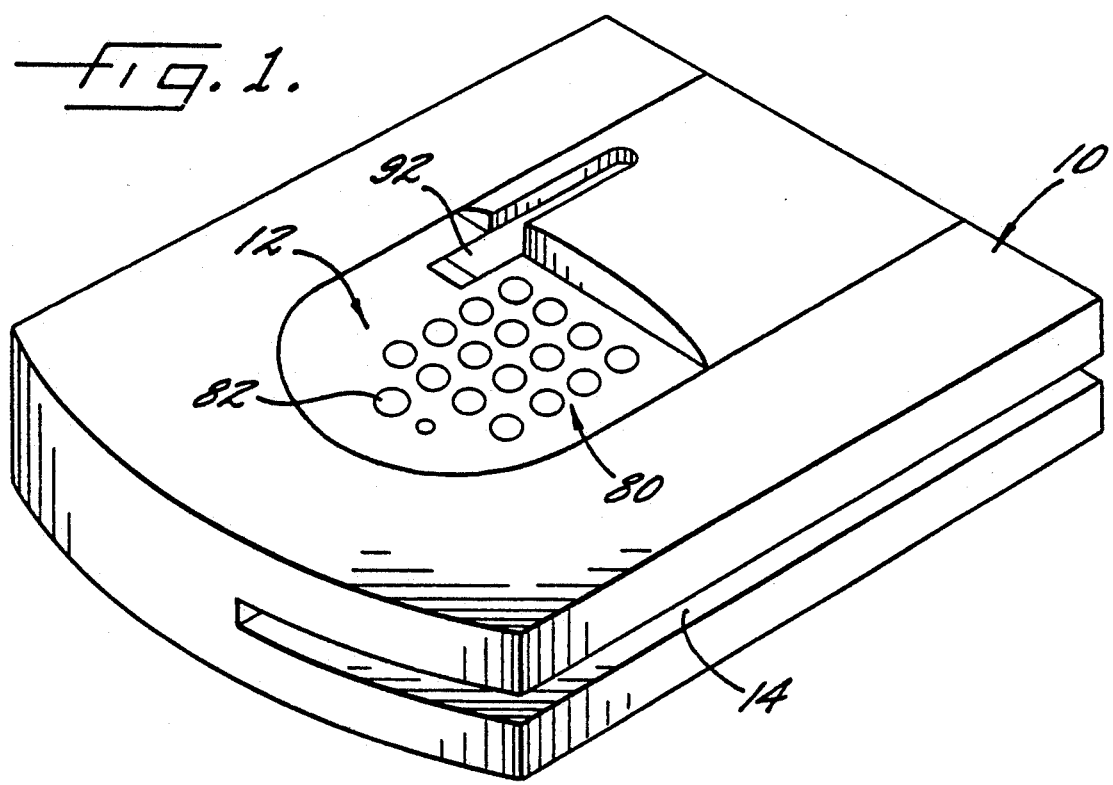
FIG. 1 is a perspective view of a preferred control unit in accordance with the present invention.

Referring to FIG. 1, a preferred control unit 10 in accordance with the present invention, beneficially includes a control panel 12 and has a side slot 14. Disposed within the control unit is a motor/roller assembly, shown in FIG. 2, which includes a motor 16 and rollers 18,20, and which has a bottom part 19 and a top part 21. Roller 18 is driven by the motor, and roller 20 is conveniently free rolling and situated above roller 18. Rollers 18,20 are spaced apart to form a slot 22, which is continuous with slot 14, and into which, with brief reference to FIGS. 6 and 7, an end 24 of a preferred compartmentalized pouch 25 in accordance with the present invention, may be inserted. If desired, roller 20 is capable of vertical translation to provide for a temporary increase in the gap of slot 22.

Figure 2:
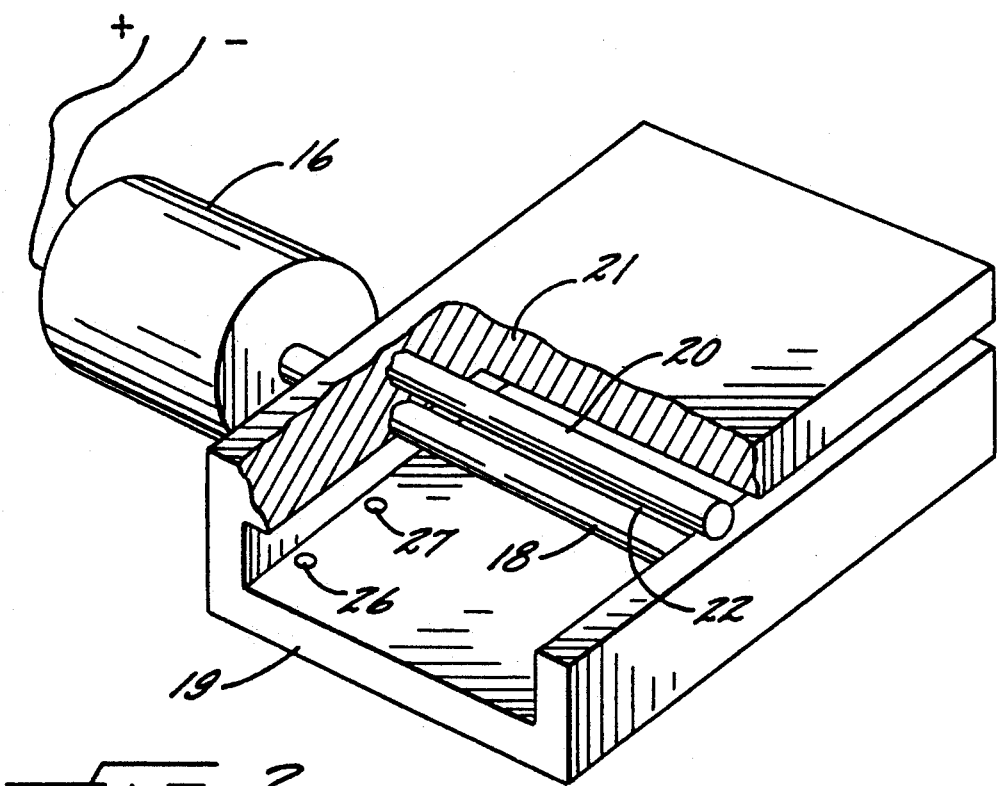
FIG. 2 is a perspective view of the motor/roller assembly of the control unit of FIG. 1, the assembly having been removed from the control unit.

The assembly of FIG. 2 also includes light sensors 26,27. Motor 16 turns lower roller 18 to begin advancing or pulling the pouch through the rollers. When optosensor 27 is blocked by the pouch, motor 16 stops.

Figure 3:
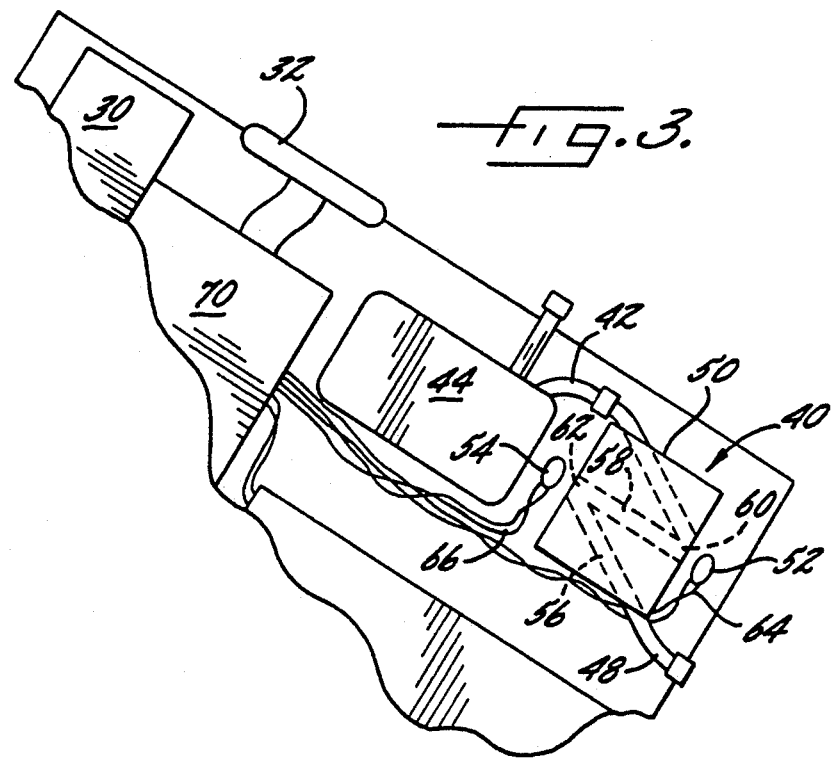
FIG. 3 is a plan view of further internal details of the control unit of FIG. 1.

With reference to FIG. 3, which shows further internal details of the control unit, control unit 10 is beneficially provided with an internal source of power 30, which is suitably a rechargeable, removable, conventional battery, and with a conventional serial port 32 for communication of the control unit with, for instance, an external computer system or a printer (not shown). Control unit 10 also advantageously includes a colorimetric analysis system 40 and, in fluid communication therewith via an outflow line 42, a beneficially removable, waste container 44 for holding processed liquid. As will be explained, the colorimetric analysis system is connectable to a pouch through an inflow line 48.

The colorimetric analysis system includes a flow cell 50, a light source 52 such as an LED, and a light sensor 54 such as a photodiode. The flow cell advantageously is made of plexiglass and has a generally z-shaped pathway 56, which includes a generally linear, central path 58. Light source 52 is conveniently situated at an end 60 of central path 58, and light sensor 54 is located at an opposite end 62 of the central path.

The volumetric capacity of the flow cell is designed for small volumes of sample. Therefore, a volumetric capacity of about 0.5 to 1.0 ml, preferably about 0.8 ml, is advantageously chosen for central path 58. Central path 58 beneficially has an extended length which provides for enhanced sensitivity for low concentrations of the target chemical species, in the case of peritoneal dialysis for $+/-10\%$ sensitivity for urea concentrations even as low as about 1 mM. Accordingly, the length of path 58 is preferably about 2.8 cm, with a length of about 2.5 to 3 cm being typically suitable. Pathway 56 is advantageously characterized by an internal diameter of about 3 mm.

Figure 4:
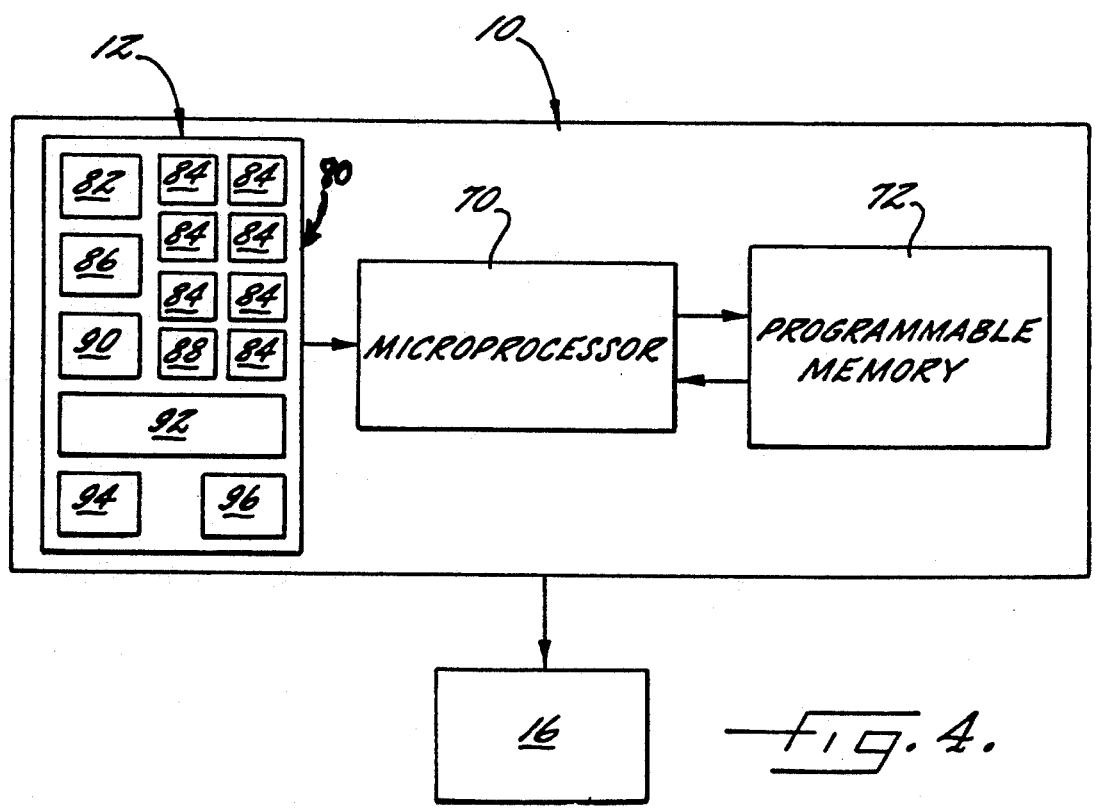
FIG. 4 is a block diagram depicting an interrelationship of parts of the control unit of FIG. 1.

Referring to FIG. 4, control unit 10 also includes a conventional microprocessor 70, which is beneficially a microcontroller, conveniently commercially available from Motorola, and includes a conventional programmable memory 72, which operatively intercommunicate with control panel 12. The control unit is equipped with appropriate software.

The control panel beneficially includes a pressure-sensitive, membrane keypad 80. The keypad includes manually actuable actuators for controlling power from battery 30, indicated at 82; for data input, indicated at 84,86; for resetting the software program to the beginning when appropriate, indicated at 88; and for data transfer via serial port 32, indicated at 90. Actuator 86 also may be used, in response to an appropriate software prompt, to initiate action of motor 16.

Control panel 12 also includes a readout panel 92, which is conveniently an LCD display, for visually communicating with a user. Display 92 may be used, for example, to request information, such as patient information, to be inputted by the user, to request the user to carry out a certain task, and to provide information to the user, for instance, to inform the user that an analysis is in the filling or incubating stage, or that dialysis is complete. The control panel further includes visual signals or alarms, conveniently LEDs, that indicate that dialysis is complete, for instance, a green light LED, and that indicate that the power is insufficient, for instance that the battery is low, indicated respectively as 94,96. Audible signals or alarms could alternatively be used. Actuator 82 beneficially includes an LED to indicate that the power is "on".

Figure 5:
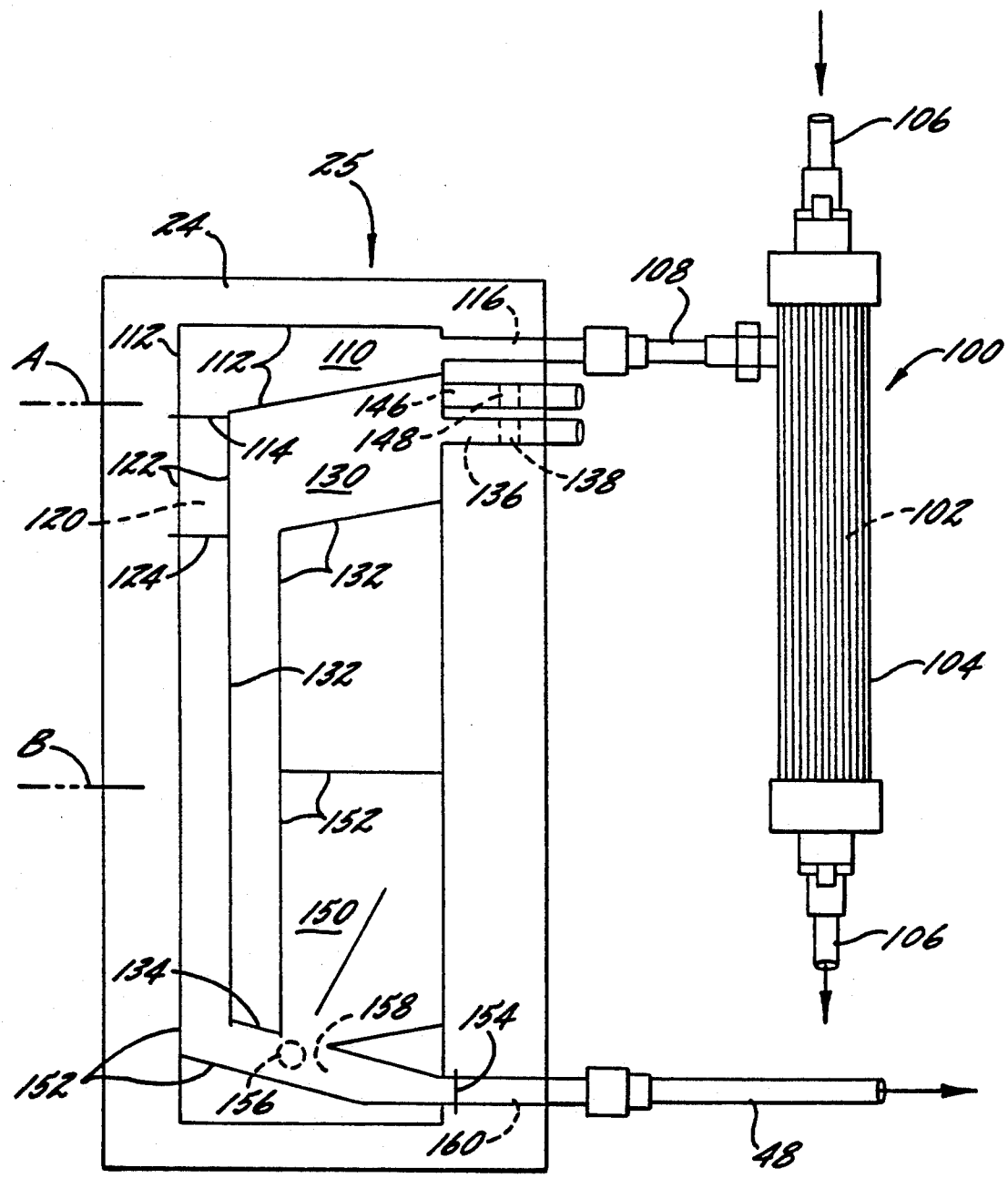
FIG. 5 is a plan view of a preferred compartmentalized pouch in accordance with the present invention, with a separator device attached.

With reference to FIG. 5, compartmentalized pouch 25 is typically connected to a separator device 100, which may be a conventional hemofilter, and which in the case of for instance, hemodialysis, typically includes membrane-forming hollow fibers 102 within a housing 104. Separator device 100 is in fluid communication with conventional tubing 106, which typically forms a circuit with a patient. A body fluid, for instance blood, is thus circulated through the separator device via tubing 106.

The walls of the membrane-forming hollow fibers of the separator device depicted in FIG. 5, have pores sized large enough for passage through the walls of a desired body fluid component such as plasma water. The desired body fluid component collects within housing 104 exterior to the fibers, prior to exit via an outlet port 108.

As an essential feature of the present invention, pouch 25 includes several pressure-compressible compartments, which will be described in detail. The pouch is advantageously formed of two layers of a suitable thermoplastic material such as PVC, and the compartments are conveniently formed in part of permanently sealed walls by use of a permanent sealing technique such as in the case of a PVC layered structure, conventional RF (Radio Frequency) welding, and in part of heat seals by use of conventional heat sealing. The heat seals are rupturable suitably by roller pressure, that is, are conveniently pressure-rupturable. It will be understood that the terms "permanently sealed" and "pressure-rupturable" or "rupturable" are relative, and that the present invention contemplates rupture of the rupturable walls but no rupture of the permanently sealed walls.

The pressure-compressible compartments may include chemicals such as suitable reagents or enzymes for the target chemical species to be analyzed. As will become clear, a portion of pouch 25 is suitably a three layered structure that includes an additional layer of the thermoplastic material selected; however, the entirety of pouch 25 could be two layered depending, for instance, upon the reagent system employed.

A pressure-compressible compartment 110 is defined by a wall portion 112 suitably formed by RF welding, and by a relatively weaker or rupturable, wall portion 114, suitably formed by heat sealing. Compartment 110 has an inlet port 116 connectable to outlet port 108 of the separator device. Compartment 110 is typically empty, that is, void, even of air or other gas. However, in the case of a pouch used for a calibration run compartment 110 contains a known concentration of urea, and compartment 110 need not be connected to a separator device.

The volumetric capacity of compartment 110 suitably determines the volume of the fluid sample provided for analysis. Alternatively, the volume to be received by compartment 110 could be metered and could be less than the volumetric capacity of the compartment. Beneficially, in accordance with the present invention, a small volume, say about 0.3 to 5 ml, of a fluid sample may be analyzed.

A pressure-compressible compartment 120 is defined by a wall portion 122 suitably formed by RF welding, and by a relatively weaker, wall portion 124, suitably formed by heat sealing, for outflow of fluid from compartment 120. Conveniently, rupturable, wall portion 114 of compartment 110 also defines compartment 120 in part. Accordingly, temporary seal 114 provides, after being ruptured, for flow of the fluid sample from compartment 110 and into a compartment 120. However, if desired, compartment 120 could be defined in part by a separately rupturable, wall portion that provides for inflow of the fluid sample after wall portion 114 has been ruptured.

Compartment 120 contains a chemical (not shown) for converting a target chemical species of the fluid sample into a reaction product which is beneficially water soluble, and which may be subsequently converted to form an analyzable, suitably colorimetrically analyzable, solution. The amount of the chemical provided within compartment 120, will depend upon factors including the volume of the fluid sample, the expected concentration range of the target chemical species, and the time to be allowed for the conversion reaction. A stoichiometric excess of the chemical vis-a-vis an upper end of the expected concentration range of the target species, may be used to provide for quantitative conversion of the target species to reaction product.

For analyzing urea, the chemical in compartment 120 may be urease enzyme, which catalytically converts urea into ammonia. In the case of a catalyst, the amount of the catalyst selected may be vis-a-vis a lower end to a midpoint of the expected concentration range of the target species. Competing considerations in selecting the amount of catalyst, include a need for sensitivity at the lower end of the range, and the time to be allowed for the conversion reaction, as a relatively greater amount of the catalyst will more rapidly effect a completion of the conversion reaction. Urease enzyme may be provided within compartment 120 either in solution or immobilized form. A nylon substrate is particularly beneficial for immobilizing urease.

With reference also to FIG. 7, pouch 25 includes compartments 130,140, which are suitably situated one directly over the other. These compartments have inlet ports 136,146, respectively, with plugs 138,148.

Pouch 25 is three-layered in the area of compartment 130. Compartment 130 is defined by a wall portion 132 suitably formed by RF welding, and by a relatively weaker, wall portion 134, suitably formed by heat sealing, for fluid outflow from compartment 130. Likewise, compartment 140 has a rupturable wall portion (not shown) for fluid outflow, which is conveniently directly beneath wall portion 134. The use of a three layered structure in which rupturable wall portions are situated one directly over the other, provides for equal volumes of fluid to be delivered simultaneously from compartments 130,140.

Compartments 130,140 contain reagents (not shown) for forming an analyzable product, suitably a colored solution suitable for colorimetric analysis, upon reaction with the reaction product formed in compartment 120. For urea analysis, a combination of colorimetric reagents is preferably utilized, these being an aqueous solution of phenol and sodium nitroprusside, and an aqueous solution of sodium hydroxide and sodium hypochlorite. Distilled water is suitably the aqueous solvent for these reagents. These reagents react with ammonia to yield a blue colored solution, in what is known as the Berthelot reaction.

Another colorimetric reagent reactive with ammonia to form a colored solution, for example thymol blue, could, of course, be used for urea analysis. When compartment 130 contains thymol blue, there is no need for compartment 140 and thus a pouch structure that is entirely two layered, may be used.

In any event, the amount of the reagent or reagents provided, will depend upon factors including the volume of the fluid sample and the expected concentration range of the target chemical species. A stoichiometric excess of the reagent or reagents vis-a-vis an upper end of the expected concentration range of the target species, may be used to provide for quantitative conversion of the reaction product to analyzable product.

The temporary seals of compartments 130,140 provide, after being ruptured, beneficially for simultaneous flow of the reagents from the respective compartments and into a compartment 150, which conveniently includes an aperture 156 in a floor 158 thereof through which flow from compartment 140 enters compartment 150. Likewise, temporary seal 124 provides for flow of typically colorless, reaction product out of compartment 120 and into compartment 150. Accordingly, compartment 150 provides for mixing of reaction product and a suitable reagent or reagents to form an analyzable product, which is suitably a colorimetrically analyzable, colored solution.

Compartment 150 is defined by a wall portion 152 suitably formed by RF welding, and by a relatively weaker, wall portion 154 for outflow of analyzable product from compartment 150. Conveniently, rupturable, wall portion 134 of compartment 130 also defines compartment 150 in part.

Compartment 150 has an outlet port 160, which provides for communication, after rupture of wall portion 154 of the pouch, advantageously with flow cell 50 via line 48. The contents of compartment 150 are thereafter analyzed, beneficially colorimetrically analyzed in the flow cell, but could be analyzed by other instrumentation.

For ease of understanding, use of a control unit and a compartmentalized pouch in accordance with the present invention, will be described in the context of analyzing for urea concentration, for instance, during hemodialysis. However, it will be understood that apparatus in accordance with the present invention has other analytical uses, and in particular other biomedical analytical uses. Other enzymes such as creatinase could be placed into a pouch compartment, for determining creatinine levels in blood.

With reference to FIGS. 1–7, at an appropriate time, programmable memory 72 communicates with microprocessor 70, and the microprocessor in response activates display 92, which indicates a urea concentration measuring time and requests insertion of pouch 25 by user. The user thereafter inserts the pouch into the side slot of control unit 10 so that end 24 of the pouch is situated between rollers 18,20.

Inlet port 116 of the pouch is connected to output port 108 of separator device 100. A patient's blood is circulated through tubing 106 and the separator device, which is suitably a hollow fiber membrane, hemofilter such as the Minifilter ® Hemofilter available from Amicon Corp.

Plasma water passes through the pores of the walls of the hollow fibers of the hemofilter and is collected in housing 104. Blood cells are larger and cannot pass through the pores, and travel through the center of the hollow fibers and pass out of the hemofilter. A predetermined volume of the plasma water, conveniently determined by the volumetric capacity of compartment 110, passes via outlet port 108 of the hemofilter and inlet port 116 of the pouch into the compartment. Suitably, the volume of plasma water is about 3 ml.

In response to an instruction displayed by display 92, the user presses actuator 86. Microprocessor 70 controls operation of battery-powered, motor 16. Under microprocessor control, the rollers now advance the pouch. As the top portion of the pouch passes through the rollers, the rollers pass over the inlet port of compartment 110, thereby blocking backflow though such port.

The rollers advance the pouch until a point A, shown in FIG. 5, is reached. The pressure of the rollers on compartment 110 compresses the pressure-compressible compartment, thereby breaking outflow-providing, heat seal 114. The motor stops when point A is reached because sensors 26,27, which operatively communicate with microprocessor 70, are blocked.

The rollers stop immediately upstream of seal 114. As a result, the plasma water is pushed by roller pressure from compartment 110 into compartment 120. The rollers now define compartment 120 in part.

Compartment 120, which is downstream of compartment 110, contains urease enzyme immobilized on a nylon substrate. The enzyme could alternatively be in solution. For a sample volume of about 3 ml, the urease enzyme suitably has an activity of about 8 units. The enzyme converts urea in the liquid sample to ammonia.

Incubation of the urea and urease enzyme takes place for a defined period of time, typically about 60 seconds. A minimum incubation time for $+/-10\%$ sensitivity is about 60 to 90 seconds. To increase sensitivity, for instance, in the case of a low concentration of the target chemical species, the time period for incubation may be extended. A maximum incubation time is typically about 5 minutes. Microprocessor 70 controls the incubation time.

For a sample volume of about 0.3 to 3 ml, compartment 130 contains a reagent in the form of about 2 ml of an aqueous solution of phenol and sodium nitroprusside, suitably in concentrations of 0.5M and 0.8 mM, respectively. Compartment 140 contains another reagent in the form of about 2 ml of an aqueous solution of sodium hydroxide and sodium hypochlorite, conveniently in concentrations of 0.5M and 30 mM, respectively. These reagents react with ammonia to yield a blue colored solution.

After the incubation step, the rollers, under microprocessor control, now advance the pouch. When a point B, shown in FIG. 5, is reached, the pressure of the rollers on compartments 120,130,140 breaks the respective outflow-providing heat seals (with temporary seal 124 being upstream of and breaking in advance of the pressure-rupturable, outflow-providing walls of compartments 130,140), and the contents of these compartments are pushed by roller pressure into compartment 150.

The rollers now define compartment 150 in part. In compartment 150, ammonia from compartment 120 and the colorimetric reagents from compartments 130,140 mix to form a blue, colorimetrically analyzable, aqueous solution. The force of the fluids exiting the respective compartments under pressure, causes them to mix very well, and very quickly in compartment 150.

Under microprocessor control, the rollers continue to advance the pouch until the entirety of pouch 25 has passed through the rollers and sensor 27 is no longer blocked. As a result, roller pressure breaks rupturable, outflow-providing heat seal 154 of compartment 150, and the blue solution of compartment 150 is pushed by roller pressure through outlet port 160 of the pouch into the plexiglass flow cell.

The microprocessor thereafter immediately activates light source 52, suitably a yellow LED, by wires 64, and light sensor 54 senses the light intensity at end 62 of pathway 58 to obtain a "blank" or baseline reading. After about 60 to 90 seconds, the microprocessor again activates light source 52 and light sensor 54, to make the analysis measurement. The intensity of light incident on the sensor is inversely proportional to the amount of urea in the liquid sample. The light intensity information is communicated by wires 66 to microprocessor 70, which based thereon, provides for computation of the urea concentration and beneficially displays the urea concentration on display 92. Advantageously, the present time and the time of any next analysis are also displayed. Subsequently, the user is prompted to remove the used pouch and, if a further analysis is required, thereafter to insert a fresh pouch.

A +/−10% sensitivity is typically found for concentrations of urea ranging from about 3 mM to about 50 mM. Similar sensitivity is generally found in the case of peritoneal dialysis for urea concentrations of about 2 mM, even as low as about 1 mM.

Accordingly, in the case of preferred pouch 25, the outflow-providing, temporary seals are sequentially ruptured: first, temporary seal 114 of compartment 110, then rupturable seal 124 of compartment 120, then the outflow-providing, rupturable seals of compartments 130,140, and finally rupturable seal 154 of the pouch.

Figure 8:
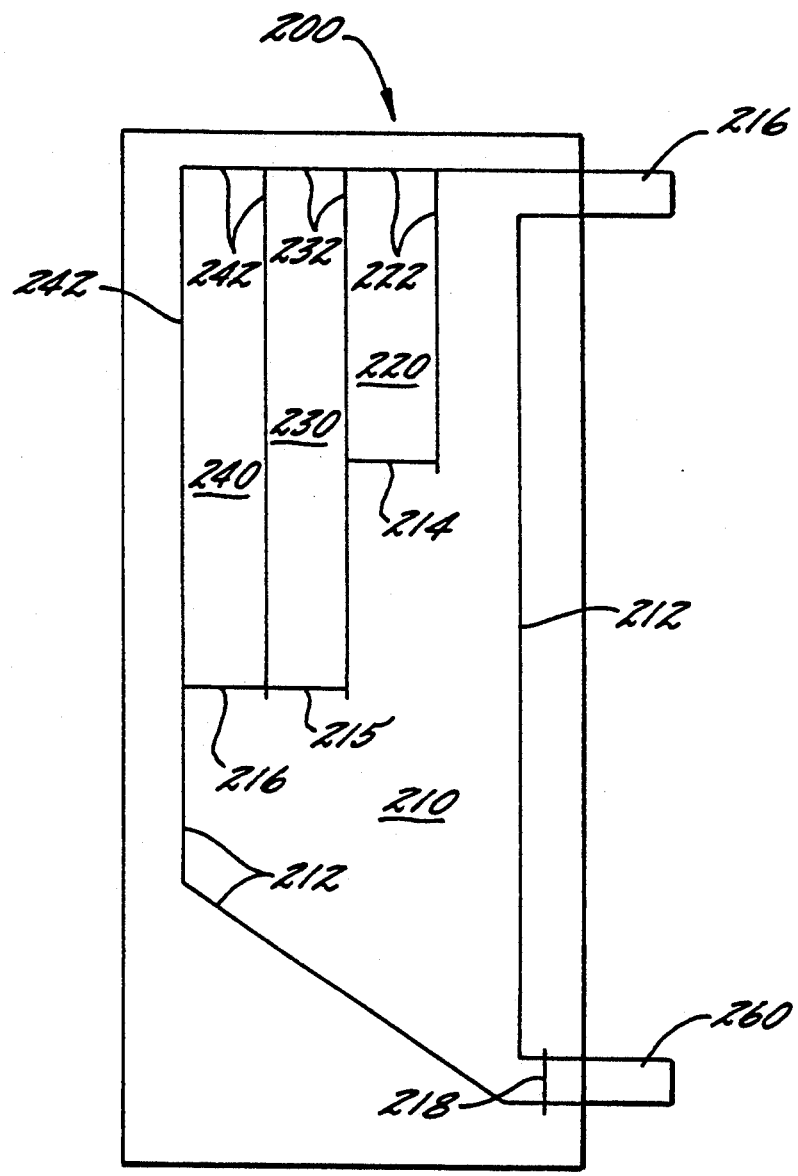
FIG. 8 is a plan view of another preferred embodiment of a compartmentalized pouch in accordance with the present invention.

FIG. 8 shows another preferred embodiment of a compartmentalized pouch in accordance with the present invention. Compared to pouch 25, this pouch is generally easier to manufacture. As this pouch is characterized by many of the features of pouch 25, the description of this pouch is generally limited, for sake of brevity, to features that are different from those of pouch 25.

With reference to FIG. 8, a two layered, compartmentalized pouch 200 is shown. A pressure-compressible compartment 210 is defined by a wall portion 212 suitably formed by RF welding, and by relatively weaker or pressure-rupturable, wall portions 214,215,216,218. Compartment 210 has an inlet port 216 for receiving a liquid sample. Like compartments 110,150, compartment 210 is typically empty, that is, void of air or other gas.

A pressure-compressible compartment 220 is defined by a wall portion 222 suitably formed by RF welding, and conveniently by relatively weaker, wall portion 214 of compartment 210 for outflow of fluid from compartment 220. Compartment 220, similar to compartment 120, contains a chemical for converting a target chemical species of the fluid sample into a reaction product. Temporary seal 214 provides, after being ruptured, for flow of the fluid from compartment 220 and into compartment 210.

Pouch 200 includes compartments 230,240, which are advantageously situated side-by-side. Compartments 230,240, like compartments 130,140, contain reagents for forming an analyzable product upon reaction with the reaction product formed in compartment 210. As in the case of pouch 25, the reagent selection may eliminate the need for compartment 240.

Compartment 230 is defined by a wall portion 232 suitably formed by RF welding, and conveniently by relatively weaker, wall portion 215 of compartment 210 for fluid outflow from compartment 230. Likewise, rupturable, wall portion 216 of compartment 210 conveniently provides for fluid outflow from compartment 240. Temporary seal 216 is conveniently in alignment with temporary seal 215. This alignment provides for the reagents to be delivered simultaneously from compartments 230,240.

As in the case of the rupturable, outflow-providing, wall portions of compartments 130,140 of pouch 25, rupturable, outflow-providing, wall portions 215,216 of compartments 230,240 are situated downstream of the rupturable, outflow-providing, wall portion of the compartment containing, in the case of a urea analysis, urease enzyme. This relative location, as well as the greater relative volumes of compartments 230,240 vis-a-vis compartment 220, prevents bursting of seals 215,216 until after seal 214 of compartment 220 has pressure-ruptured.

The rupturable, wall portions of compartments 230,240 provide, after being ruptured, beneficially for simultaneous flow of the reagents from the respective compartments and into compartment 210, which will typically contain colorless, reaction product. Accordingly, compartment 210 also provides for mixing of reaction product and a suitable reagent or reagents to form an analyzable product, which is suitably a colorimetrically analyzable, colored solution.

Compartment 210 includes temporary seal 218 for outflow of analyzable product from compartment 210. Compartment 210 has an outlet port 260, which provides for communication, after rupture of wall portion 218 of the pouch, advantageously with flow cell 50 via line 48 (both shown in FIG. 3). The contents of compartment 210 are thereafter analyzed, suitably colorimetrically analyzed in the flow cell, but could be subjected to another type of analysis by other instrumentation.

Accordingly, in the case of preferred pouch 200, outflow-providing, temporary seals are sequentially ruptured as follows: first, seal 214, which conveniently forms a portion of the wall of compartment 220, then seals 215,216, which conveniently form a portion of the wall of compartments 230,240, respectively, and finally seal 218, which is downstream of the other seals.

By the apparatus described, a single fluid sample can be analyzed for a target chemical species. However, it will be understood that a compartmentalized pouch in accordance with the present invention, may be designed to be useful for the analysis of multiple samples.

Having described the invention in detail and by reference to preferred embodiments thereof, it will be apparent that modifications and variations are possible without departing from the scope of the invention defined in the appended claims. Several changes or modifications have been briefly mentioned for purposes of illustration.

I claim:

1. Microprocessor-based, self-contained, biomedical monitoring apparatus comprising a control unit comprising a microprocessor and programmable memory in operative communication with means for data input and means for informing as to an analytical value obtained; a microprocessor-controlled, pressure-exerting assembly; an internal power source for said control unit and said pressure-exerting assembly; a compartmentalized, analysis device having an inlet coupled to a source of multiple samlpes in the form of a separate device, said separate device being an exteriorly located, blood plasma-separating device, and comprising a compressible reagent chamber and compressible reaction chamber, said reagent chamber being adapted for fluid communication with said reaction chamber, which has outflow means in fluid communication with a flow through, analysis cell for microprocessor-controlled delivery of analyzable liquid to said analysis cell; and analytical sensor means situated adjacent said analysis cell, said microprocessor being in operative communication with said analytical sensor means for analysis of said analyzable liquid.

2. The microprocessor-based, monitoring apparatus of claim 1, wherein said analytical sensor means is photometric analysis means.

3. The microprocessor-based, monitoring apparatus of claim 1, wherein said flow through, analysis cell is in fluid communication with a waste container for said analyzable liquid.

4. A method for microprocessor-based, biomedical monitoring comprising providing a self-contained, biomedical monitoring apparatus comprising a control unit comprising a microprocessor and programmable memory in operative communication with means for data input and means for informing as to an analytical value obtained, a microprocessor-controlled, pressure-exerting assembly, and a compartmentalized, analysis device having compressible chambers, an inlet, and a conduit for delivery of an analyzable liquid to a flow through, analysis cell; coupling said inlet to a source of multiple samples in the form of a separate device, said separate device being an exteriorly located, blood plasma-separating device; thereafter, admitting a selected volume of plasma into a compressible reaction chamber of said analysis device; under microprocessor control and with said inlet coupled to said blood plasma-separating device, providing for communication between a compressible reagent chamber and said compressible reaction chamber, and delivering a suitable amount of a reagent into said compressible reaction chamber; thereafter, under microprocessor control, providing for fluid communication between said compressible reaction chamber and said analysis cell, and delivering said analyzable liquid into said analysis cell; and thereafter, under microprocessor control, analyzing said analyzable liquid in said analysis cell, and informing as to the analytical value obtained.

5. The microprocessor-based, biomedical monitoring method of claim 4, further comprising, under microprocessor control, passing said analyzable liquid to a waste container.

6. The microprocessor-based, biomedical monitoring method of claim 4, wherein photometric analysis of said analyzable liquid is used.

7. The microprocessor-based, biomedical monitoring method of claim 4, wherein said analysis device comprises a second compressible reagent chamber, and wherein said method further comprises, under microprocessor control, providing for communication between said second reagent chamber and said compressible reaction chamber.

* * * * *